United States Patent [19]

Gilman et al.

[11] Patent Number: 4,973,599
[45] Date of Patent: Nov. 27, 1990

[54] PHENYLTHIOHETEROCYCLIC DERIVATIVES

[75] Inventors: Norman W. Gilman, Wayne; Wen Y. Chen, Nutley, both of N.J.

[73] Assignee: Hoffman-La Roche Inc., Nutley, N.J.

[21] Appl. No.: 323,583

[22] Filed: Mar. 14, 1989

[51] Int. Cl.⁵ ................. C07D 233/84; A61K 31/415
[52] U.S. Cl. ....................... 514/398; 514/274; 514/369; 548/337; 548/182; 548/186; 544/315; 544/318
[58] Field of Search ............. 514/274, 369, 398; 544/315, 318; 548/182, 186, 337

[56] References Cited
PUBLICATIONS

Noguchi et al., Chemical Abstracts, vol. 70, Entry 77873q (1969).
Henry, Chemical Abstracts, vol. 68, Entry 1051952 (1968).
Niedballa et al., Chemical Abstracts, vol. 96, Entry 181284w (1982).
van Zwieten et al., Chemical Abstracts, vol. 57, Entry 12464h (1962).
van Zwieten et al., C.A. 57; 16547f (1962).
van Zwieten et al., C.A. 57: 17134(c) (1962).
Bouin–Roubaud et al., Can. J. Chem. vol. 59, pp. 2883–2890 (1981).
Delarge et al., Eur. J. Med. Chem. Chim. Ther., (1984) 19 No. 6, 559–565.

*Primary Examiner*—John M. Ford
*Attorney, Agent, or Firm*—George M. Gould; Bernard S. Leon; William G. Isgro

[57] ABSTRACT

Compounds of the formula

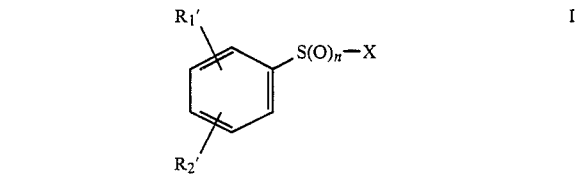

wherein n is a integer of 0 to 2; $R_1'$ and $R_2'$ are, independently, hydrogen, halogen, trifluoromethyl, lower alkoxy or lower alkyl; and X is pyrimidinyl, thiazolyl or

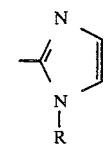

wherein R is hydrogen, lower alkyl, aryl or ar-lower alkyl; provided that at least one or $R_1'$ and $R_2'$ is other than hydrogen,
and their pharmaceutically acceptable acid addition salts, and an anti-inflammatory method utilizing a compound of the formula

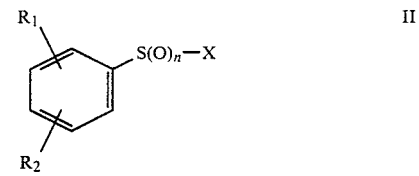

wherein n is an integer of 0 to 2; $R_1$ and $R_2$ are, independently, hydrogen, halogen, trifluoromethyl, nitro, amino, lower alkylamino, di-lower-alkylamino, lower alkoxy or lower alkyl; and X is pyrimidinyl, thiazolyl or wherein R is hydrogen, lower alkyl, aryl or ar-lower alkyl;
and their pharmaceutically acceptable acid addition salts, are described.

11 Claims, No Drawings

PHENYLTHIOHETEROCYCLIC DERIVATIVES

BRIEF SUMMARY OF THE INVENTION

The invention relates to compounds of the formula

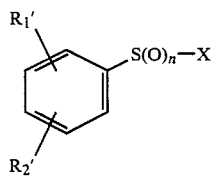

wherein n is an integer of 0 to 2; $R_1'$ and $R_2'$ are, independently hydrogen, halogen, trifluoromethyl, lower alkoxy or lower alkyl; and X is pyrimidinyl, thiazolyl or

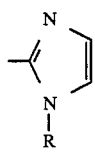

wherein R is hydrogen, lower alkyl, aryl or ar-lower alkyl; provided that at least one of $R_1'$ and $R_2'$ is other than hydrogen, and their pharmaceutically acceptable acid addition salts.

In another aspect, the invention relates to an anti-inflammatory method utilizing compounds of the formula

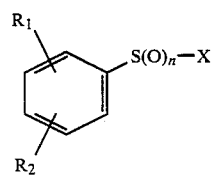

wherein n is an integer of 0 to 2; $R_1$ and $R_2$ are, independently, hydrogen, halogen, trifluoromethyl, nitro, amino, lower alkylamino, di-lower-alkylamino, lower alkoxy or lower alkyl; and X is pyrimidinyl, thiazolyl or

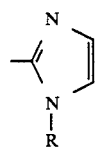

wherein R is hydrogen, lower alkyl, aryl or ar-lower alkyl:

and their pharmaceutically acceptable acid addition salts.

The compounds of formula I are useful as agents for the treatment of inflammatory diseases such as arthritis, inflammatory bowel diseases such as colitis, skin diseases such as psoriasis, and bronchopulmonary diseases such as asthma.

DETAILED DESCRIPTION OF THE INVENTION

As used herein, the term "lower alkyl" denotes a straight or branched chain saturated hydrocarbon radical containing 1 to 8 carbon atoms, for example, methyl, ethyl, propyl, isopropyl, butyl, t-butyl, neopentyl, pentyl, heptyl, octyl and the like. The term "lower alkoxy" denotes an ether derivative of a straight or branched chain saturated hydrocarbon containing 1 to 8 carbon atoms, for example, methoxy, ethoxy, propoxy, isopropoxy, butoxy, t-butoxy, neopentoxy, heptoxy, octoxy and the like. The term "halogen" denotes all the halogens, that is, bromine, chlorine, fluorine, and iodine. The term "aryl" or "ar" denotes phenyl or phenyl bearing one or two substituents independently selected from the group consisting of halogen, trifluoromethyl, lower alkyl, lower alkoxy, nitro, amino, lower alkylamino and di-lower alkylamino. The term "ar-lower alkyl" denotes a straight or branched chain lower alkyl group in which one or more of the hydrogen atoms have been replaced by an aryl group, for example, benzyl, phenethyl and the like.

Examplary of pyrimidinyl are 2-pyrimidinyl, 4-pyrimidinyl and 5-pyrimidinyl. Examplary of thiazolyl are 2-thiazolyl, 4-thiazolyl and 5-thiazolyl. Examples of lower alkylamino groups are methylamino, ethylamino, propylamino, butylamino and the like. Examples of di-loweralkylamino groups are dimethylamino, diethylamino, dipentylamino, dihexylamino dioctylamino and the like.

The invention relates to compounds of the formula

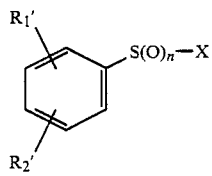

wherein $R_1'$ and $R_2'$ are, independently, hydrogen, halogen, trifluoromethyl, lower alkoxy or lower alkyl; and X is pyrimidinyl, thiazolyl or

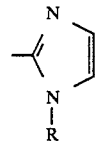

wherein R is hydrogen, lower alkyl, aryl or ar-lower alkyl; provided that at least one of $R_1'$ and $R_2'$ is other than hydrogen, and their pharmaceutically acceptable acid addition salts.

In another aspect, the invention relates to an anti-inflammatory method utilizing compounds of the formula

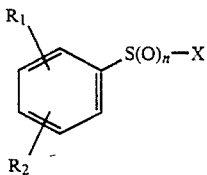

wherein $R_1$ and $R_2$ are, independently, hydrogen, halogen, trifluoromethyl, nitro, amino, lower alkylamino, di-lower-alkylamino, lower alkoxy or lower alkyl; and X is pyrimidinyl, thiazolyl or

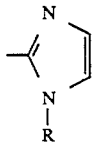

wherein R is hydrogen, lower alkyl, aryl or ar-lower alkyl;

and their pharmaceutically acceptable acid addition salts.

A preferred group of compounds of formula I are those wherein one or both of $R_1$ and $R_2$ are independently, lower alkoxy, halogen or trifluoromethyl and X is pyrimidinyl and

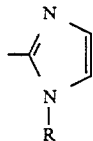

wherein R is as previously described.

A more preferred group of compounds of formula I are those wherein one or both of $R_1$ and $R_2$ are, independently halogen or trifluoromethyl and X is

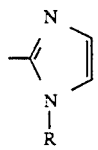

wherein R is lower alkyl.

Preferred compounds of formula I of the invention:
2-[(2-chlorophenyl)thio]-1H-imidazole;
2-[(4-chlorophenyl)thio]-1H-imidazole; and
2-[(4-chlorophenyl)thio]-pyrimidine.

Examplary of compounds of formula I of the invention are:

2[(4-Methyl-2-nitrophenyl)thio]-1-methyl-1H-imidazole;
1-n-Butyl-2-[(2-chloro-4-methylphenyl)thio]-1H-imidazole;
2-[(2-Chloro-4-methylphenyl)thio]-1-phenyl-1H-imidazole;
2-[(4-Chloro-3-methylphenyl)thio]-1-methyl-1H-imidazole;
2-[[2-Chloro-(4-methylamino)phenyl]thio]-1-methyl-1H-imidazole;
2-[[4-Chloro-(2-methylamino)phenyl]thio]-1-methyl-1H-imidazole;
2-[[2-Chloro-(4-n-propylamino)phenyl]thio-1-methyl-1H-imidazole:
2-[[(2-Trifluoromethyl)-(4-methylamino)phenyl]thio]-1-methyl-1H-imidazole;
2-[[2-Chloro-(4-dimethylamino)phenyl]thio]-1-methyl-1H-imidazole;
2-[[(2-Dimethylamino)-4-methoxyphenyl]thio]-1-methyl-1H-imidazole;
2-[[2-Chloro-(4-diethylamino)phenyl]thio]-1-methyl 1H-imidazole;
2-[[(4-Trifluoromethyl)phenyl]thio]pyrimidine;
2-[[(2-Dimethylamino)phenyl]thio]pyrimidine;
2-[[(4-Methylamino)phenyl]thio]pyrimidine;
2-[[4-Chloro-(2-trifluoromethyl)phenyl]thio]pyrimidine;
2-[[(4-Dimethylamino)phenyl]thio]thiazole; and
2-[[4-Methyl-2-(trifluoromethyl)phenyl]thio]thiazole.

The compounds of formula II, which include the compounds of formula I, can be prepared as hereinafter described in Reaction Schemes I-III.

Reaction Scheme I

Reaction Scheme I

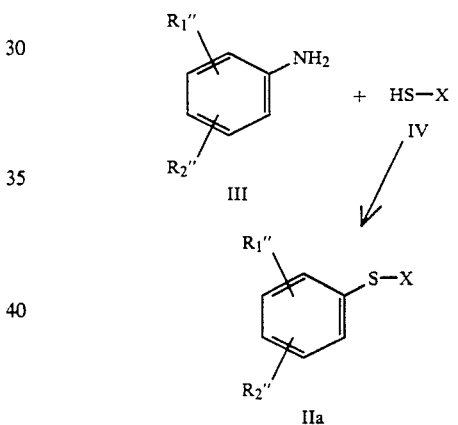

wherein X is as previously described and $R_1''$ and $R_2''$ are independently, hydrogen, halogen, trifluoromethyl nitro, lower alkylamino, di-loweralkylamino, lower alkoxy or lower alkyl.

In Reaction Scheme I, a compound of formula III, which are known compounds or can be prepared according to known procedures, can be diazotized using sodium nitrite in acidic medium, a standard Sandmeyer type reaction. The diazonium solution is then added to a compound of formula IV which are known compounds or can be prepared according to known procedures, in an acidic solution. The reactions can be carried out at temperatures in the range of −20° C. to 50° C. with −5° C. to 25° C. being preferred. The acid is neutralized by the addition of an inorganic base such as, ammonium hydroxide, and the reaction product is extracted with an organic solvent such as diethyl ether ethyl acetate or dichloromethane to yield the corresponding compound of formula IIa. The resulting compound of formula IIa can be recovered utilizing standard procedures, for example, crystallization, precipitation, chromatography and the like.

REACTION SCHEME II

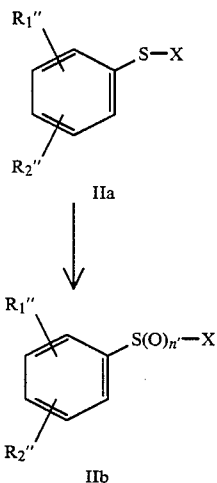

wherein X, $R_1''$ and $R_2''$ are as previously described, and n' is 1 or 2.

In Reaction Scheme II, a compound of formula IIa is treated with one molar equivalent of an organic peracid such as metachloro perbenzoic acid if a compound of formula IIb, wherein n' is one (1), is to be prepared, and two molar equivalents, if a compound of formula IIb, wherein n' is two (2), is to be prepared, in an inert organic solvent such as dichloromethane at temperatures in the range of $-20°$ C. to $100°$ C. The resulting product of formula IIb is isolated from the reaction mixture by the addition of an inorganic base, such as sodium hydroxide followed by extraction with an organic solvent such as diethyl ether, ethyl acetate or dichloromethane and recovery by standard procedures, for example, crystallization, precipitation, chromatography and the like.

REACTION SCHEME III

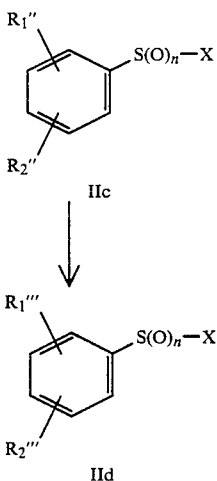

wherein n, $X_1$, $R_1''$ and $R_2''$ are as previously described, provided that one or both of $R_1''$ and $R_2''$ are nitro, and wherein X, $R_1'''$ and $R_2'''$ are independently, hydrogen, halogen, trifluoromethyl, amino, lower alkylamino, di-lower alkylamino, lower alkoxy or lower alkyl, provided that at least one of $R_1'''$ or $R_2'''$ is amino.

In Reaction Scheme III, a compound of formula IIc, which can be prepared as described in Reaction Scheme I, is reacted whereby the nitro group is transformed into an amino group to yield the corresponding compound of formula IId. The conversion to the amino group can be carried out by standard reduction methods such as use of stannous chloride or catalytic hydrogenation. A stannous chloride reduction can be carried out in acidic medium at temperatures in the range of $0°$ C. to $50°$ C. to yield the corresponding compound of formula IId. The resulting compound of formula IId is isolated by neutralizing the acid with an inorganic base followed by extraction with an organic solvent such as diethyl ether, ethyl acetate or dichloromethane and can be recovered utilizing standard procedures for example, crystallization precipitation, chromatography and the like. If desired, an amino group can be replaced by a halogen group utilizing standard procedures for the diazotization of an amine, i.e. sodium nitrite, acidic medium, temperatures of from $-10°$ C. to $50°$ C. followed by treatment with the appropriate halide such as cuprous chloride cuprous bromide or potassium iodide.

REACTION SCHEME IV

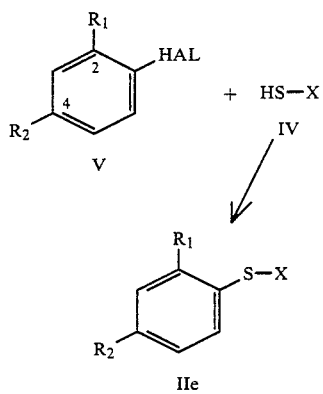

wherein X, $R_1$ and $R_2$ are as previously described, provided that one of $R_1$ or $R_2$, or both, are nitro.

In Reaction Scheme IV, a compound of formula V, which are known compounds or can be prepared according to known procedures, is treated with a mercaptoheterocyclic compound of Formula IV in the presence of a base such as sodium hydride sodium methoxide, or sodium hydroxide. The reaction can be carried out in an organic solvent such as N,N-dimethylformamide, lower alkanol such as methanol or ethanol, or dimethyl sulfoxide at temperatures ranging from room temperature to $150°$ C. to yield the corresponding compound of formula IIe. A compound of formula IIe can be isolated by quenching the reaction mixture with water or sodium chloride solution followed by extraction with an organic solvent such as diethyl ether, ethyl acetate or dichloromethane, and can be recovered utilizing standard procedures for example, crystallization precipitation chromatography and the like.

The compounds of formula I and formula II form acid addition salts and such salts are also within the scope of this invention. Thus the compounds of formula I and formula II form pharmaceutically acceptable addition salts with, for example, both pharmaceutically acceptable organic and inorganic acids, such as acetic acid, succinic acid, formic acid, methanesulfonic acid, p-toluene-sulfonic acid, hydrochloric acid, nitric acid, phosphoric acid, sulfuric a id and the like.

The compounds of formula I are useful as agents for the treatment of inflammatory diseases such as arthritis; inflammatory bowel disease such as colitis, skin diseases such as psoriasis; and bronchopulmonary diseases such as asthma.

Carrageenan Pleurisy Test (In Vivo)

The animals utilized in these studies were male Lewis rats (Charles River Breeding Laboratories) weighing between 230–250 g. Carrageenan (CG) pleurisy was induced by injecting 0.2 ml of 1% lambda carrageenan (Sigma Lot #60F-0652) dissolved in sterile, pyrogen free, saline into the right pleural cavity of the rat using a 26 gauge (⅜") intradermal needle. Compounds suspended in aqueous suspending vehicle (ASV, 0.5% carboxymethylcellulose containing 0.9% NaCl, 0.37% Tween 80 and 0.85% benzyl alcohol) were administered by intubation 1 hour before CG injection for the 5 hour treatment period and 1 hour before and 5 hours after CG injection for the 24 hour treatment period. Drugs were administered at doses which, on the basis of preliminary experiments, would significantly suppress the development of CG-induced pleurisy under our experimental conditions.

At 5 or 24 hours after CG injection, the rats were killed by decapitation, exsanguinated, and the pleural cavity exposed by cutting the ribs on both sides of the sternum. The exudate fluid was removed from the pleural cavity with disposable plastic pipettes and its volume quantitated. The pleural cavity was then washed once with phosphate buffered saline containing fetal bovine serum (1:1) and the washings combined with the exudate. The total number of cells in the pleural cavity was quantitated using a Coulter Counter (Model ZM) adjusted to exclude any contaminating RBC. (Published in "Plant Flavonoids in Biology & Medicine: Biochemical, Pharmacological and Structure-Activity Relationships" p. 231–242 (1986) Alan R. Liss, Inc.)

Data for the compounds of this invention in this test are reported in Table I.

TABLE I

| Compound | $R_1$ | $R_2$ | X | Dose, mg/kg | Exudate Volume % Reduction |
|---|---|---|---|---|---|
| 1 | 2-$NO_2$ | H | 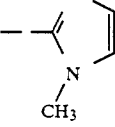 | 30 | 59 |
| 2 | 2-Cl | H | 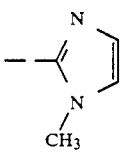 | 30 | 58 |
| 3 | 4-Cl | H | 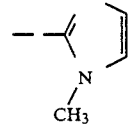 | 30 | 60 |
| 4 | 4-$NO_2$ | H | 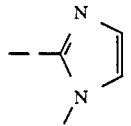 | 100 | 83 |
| 5 | 4-Cl | | 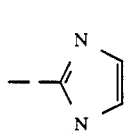 | 100 | 58 |
| 6 | 2-Cl | 6-Cl | 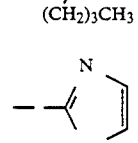 | 30 | 54 |
| 7 | 2-$NO_2$ | 4-Cl | 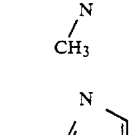 | 30 | 50 |
| 8 | 4-$NO_2$ | H | 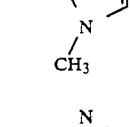 | 30 | 59 |
| 9 | 4-$NO_2$ | H | 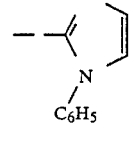 | 30 | 35 |
| 10 | 2-Cl | H | 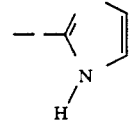 | 30 | 32 |
| 11 | 4-Cl | H | 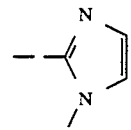 | 30 | 59 |
| 12 | 4-$CF_3$ | H | 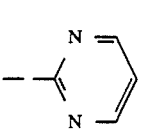 | 30 | 50 |

TABLE I-continued

| Compound | R₁ | R₂ | X | Dose, mg/kg | Exudate Volume % Reduction |
|---|---|---|---|---|---|
| 13 | 2-Cl | H | 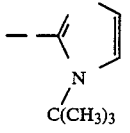 | 30 | 63 |
| 14 | 2-Cl | 4-I | 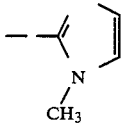 | 47 | 39 |
| 15 | 2-CF₃ | 4-Cl | 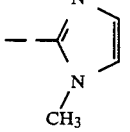 | 30 | 36 |
| 16 | 2-Cl | H | 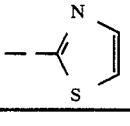 | 40 | 50 |

A compound of formula I or formula II or a salt thereof or a composition containing a therapeutically effective amount of a compound of formula I or formula II or a salt thereof can be administered by methods well known in the art. Thus, a compound of formula I or formula II or a salt thereof can be administered either singly or with other pharmaceutical agents, orally, parenterally, rectally or by inhalation, for example, in the form of an aerosol, micropulverized powder or nebulized solution. For oral administration the described compounds can be administered in the form of tablets, capsules, for example, in admixture with talc, starch, milk sugar or other inert ingredients, that is, pharmaceutically acceptable carriers, in the form of aqueous solutions, suspensions, elixirs or aqueous alcoholic solutions, for example, in admixture with sugar or other sweetening agents, flavoring agents, colorants, thickeners and other conventional pharmaceutical excipients, or beadlets for oral administration. For parenteral administration, the desired compound can be administered in solutions or suspension, for example as an aqueous or peanut oil solution or suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, that is one which on activation releases a predetermined effective dose of the aerosol composition. For rectal administration the desired compound can be administered in the form of suppositories utilizing an inert carrier material cocoa butter and the like. For topical administration, the described compounds can be incorporated into ointments, creams, lotions, gels, and the like.

In general, the solutions, ointments and creams which are useful in accordance with this invention include formulations having absorbable, water soluble or emulsion-type bases, such as petrolatum, lanolin, polyethylene glycols, or the like.

Suitable solutions will contain the compounds of formula I or formula II or their salts dissolved in a pharmaceutically acceptable solvent, such as polyethylene glycol, or the like.

Suitable lotions include, true solutions to aqueous or hydroalcoholic formulations containing finely divided particles. Lotions can contain suspending or dispersing agents such as cellulose derivatives, for example, methyl cellulose, ethyl cellulose, or the like. Gels will typically be semi-solid preparations made by gelling a solution or suspension of a compound of formula I or formula II in a suitable hydrous or anhydrous vehicle, using a gelling agent such as a carboxy polymethylene, or the like, and thereafter neutralizing it to proper consistency with an alkali metal hydroxide, for example, sodium hydroxide, and an amine, for example, polyethylenecocoamine. Topical pharmaceutical compositions containing a compound of formula I or formula II or a salt thereof can also be formulated to include conventional ingredients such as preservatives, stabilizers, wetting agents, emulsifying agents, buffers, and the like, in conventional amounts adjusted for particular requirements and which are readily determinable by those skilled in the art.

In the practice of the invention, the dose of a compound of formula I or formula II or a salt thereof to be administered and the frequency of administration will be dependent on the potency and duration of activity of the particular compound of formula I or formula II or salt to be administered and on the route of administration, as well as the severity of the condition, age of the mammal to be treated and the like. Oral doses of a compound of formula I or formula II or a salt thereof contemplated for use in practicing the invention are in the range of from about 5 to about 100 mg/kg per day.

The Examples which follow further illustrate the invention. All temperatures are given in degrees Centigrade, unless otherwise stated.

EXAMPLE I

1-Methyl-2-[(2-nitrophenyl)thio]-1H-imidazole

To a slurry of 0.8 g (20 mmoles) of sodium hydride (60% dispersion in mineral oil) in 10 ml of N,N-dimethylformamide, stirred in an ice bath, and under a nitrogen atmosphere, was added dropwise a solution of 2.28 g (20 mmoles) of 2-mercapto-1-methylimidazole in 5 ml of N,N-dimethylformamide. After the evolution of hydrogen gas had ceased, the ice bath was removed and the reaction mixture stirred at room temperature for 0.5 hours. To the reaction was added, dropwise, a solution of 2.82 g (20 mmoles) of 1-fluoro-2-nitrobenzene in 10 ml of N,N-dimethylformamide. After stirring at room temperature for 16 hours, the mixture was poured into a saturated sodium chloride solution (100 ml) and extracted with dichloromethane. The organics were dried and the solvents were removed in vacuo. The resulting yellow solid was triturated with ether and collected by filtration to give 3.5 g (74%) of product as yellow prisms, mp 117°–119° C.

EXAMPLE 2

1-Methyl-2-[(2-nitrophenyl)thio]-1H-imidazole hydrochloride dihydrate

The product obtained in Example 1 was converted to the hydrochloride salt by treatment in a mixture of ether and dichloromethane with gaseous hydrogen chloride. The product was obtained as yellow prisms, mp 160°–165° C.

EXAMPLE 3

1-Methyl-2-[(4-nitrophenyl)thio]-1H-imidazole

The same procedure described in Example 1 was used except that 1-fluoro-4-nitrobenzene was used instead of 1-fluoro-2-nitrobenzene. The product was obtained as yellow prisms, mp 120°–121° C.

EXAMPLE 4

4-(1-Methyl-1H-imidazole-2-yl)thio]]benzenamine

To a solution of 1.4 g (6 mmols) of the product from Example 3 in 15 ml of glacial acetic acid was added a solution of 6.8 g (30 mmoles) of stannous chloride dihydrate in 20 ml of 6N hydrochloric acid and 30 ml of glacial acetic acid. After stirring at room temperature for 16 hours, the reaction mixture was cooled in an ice bath and partially neutralized with a solution of 6 g of sodium hydroxide in 30 ml of water. The mixture was concentrated in vacuo to remove most of the acetic acid and the residues was treated with concentrated ammonium hydroxide until basic. The mixture was filtered and the solid was washed with water. The filtrates were extracted with dichloromethane and combined with the collected solid. The organic solution was dried and concentrated. The residue was chromatographed on silica gel using dichloromethane/methanol (9:1 by volume) to elute the product. The fractions containing the product were combined and concentrated to give a solid which was triturated with ether and collected by filtration to give the product (0.6 g. 50%) as off-white prisms mp 115°–117° C.

EXAMPLE 5

2-[(1-Methyl-1H-imidazole-2-yl)thio]]benzenamine

Utilizing the procedure given in Example 4, and using the product obtained in Example 1 as starting material, the product was obtained as off-white prisms in 75% yield mp 118°–120° C.

EXAMPLE 6

2-[(2-Chlorophenyl)thio]-1H-imidazole

Method A. To a solution of 24.6 g (0.12 mole) of the product from Example 5 in 180 ml of 3N hydrochloric acid and 180 ml of glacial acetic acid (stirred in an ice bath) was added dropwise over 20 minutes, a solution of 8.4 g (0.12 mole) of sodium nitrite in 24 ml of water. This mixture was then added in portions over 20 minutes to a solution (at −5° C.) of 35 g (0.35 mole) of cuprous chloride in 325 ml of 6N hydrochloric acid. The reaction mixture was then stirred at room temperature for 1 hour and then cooled in an ice bath. The solid was collected by filtration and combined with the solid obtained from an identical, duplicate run. The solid was partitioned with ethyl acetate and ammonium hydroxide and the organics were combined, dried and concentrated to give 31.4 g (58%) of the product as a yellow oil. The oil was chromatographed on silica gel and eluted with ethyl acetate. The fractions containing the product were combined and concentrated to give 24.6 g of product as an oil which crystallized upon standing at −10° C. The product was obtained as off-white prisms, mp 37°–39° C.

Method B. A mixture of 0.6 g of zinc powder was stirred for 20 minutes at 60° C. with 25 ml of 1N sulfuric acid and then filtered. To the filtrate was added 0.35 g of cuprous oxide followed by 0.9 g (7.8 mmoles) of 2-mercapto-1-methylimidazole. 2-Chloroaniline (1 g, 7.8 mmoles) in 36 ml of 1N sulfuric acid was diazotized by cooling in an icebath followed by the dropwise addition of a solution of 0.57 g (8.2 mmoles) of sodium nitrite in 5 ml of water. The diazonium solution was then added over 30 minutes, and at 0° C. to the above solution of 2-mercapto-1-methylimidazole. The mixture was stirred at 0° for 2 hours and then at room temperature for 2 hours. The mixture was decanted and made basic by treatment with ammonium hydroxide and extracted with ether. The organics were washed with saturated sodium chloride solution, dried and concentrated. The residue was dissolved in a small amount of dichloromethane and filtered through silica gel using ether as the eluent. The fractions containing the product were combined and concentrated to give 1.1 g (63%) of the product, identical to the product obtained in Method A.

EXAMPLE 7

2-[(2-Chlorophenyl)thio]-1H-imidazole hydrochloride

The product from Example 6 was dissolved in ether and treated with gaseous hydrogen chloride. The product was obtained as off-White prisms, mp 165°–170° C.

EXAMPLE 8

2-[(4-Chlorophenyl)thio]-1H-imidazole

Using the procedure given in Example 6 and starting with the product from Example 4. there was obtained a 65% yield of the product as off-white prisms, mp 86°–88° C.

EXAMPLE 9

2-[(4-Chlorophenyl)thio]-1H-imidazole hydrochloride

The product from Example B was dissolved in ether and treated with gaseous hydrogen chloride. The product was collected by filtration, washed with ether and air-dried and was obtained as off-white prisms, mp 180°–185° C.

EXAMPLE 10

2-[(4-Chlorophenyl)sulfinyl-1-methyl-1H-imidazole

A solution of 450 mg (2 mmoles) of the product from Example 8 in 50 ml of dichloromethane was treated with 360 mg (2.1 mmoles of meta-chloroperbenzoic acid. After stirring at room temperature for 40 minutes, the mixture was poured into ammonium hydroxide and extracted with dichloromethane. The organics were combined, dried and concentrated. The residue was chromatographed on silica gel using ethyl acetate as the eluent. The fractions containing the product were combined and concentrated. The residue was crystallized from petroleum ether (bp 30°–60° C.) to give 300 mg (63%) of the product as light tan prisms, mp 96°–97° C.

EXAMPLE 11

2-[(4-Chlorophenyl)sulfonyl-1-methyl-1H-imidazole

To a solution of 0.9 g (4 mmoles) of the product from Example 8 in 100 ml of dichloromethane, was added 1.7 g (10 mmoles) of meta-chloroperbenzoic acid. After stirring at room temperature for 16 hours the product was isolated following the procedure given in Example 10 and gave, after column chromatography, 0.7 g (68%) of the product as off-White prisms, mp 164°-166° C.

EXAMPLE 12

1-n-Butyl-2-[(4-nitrophenyl)thio]-1H-imidazol hydrochloride

To a solution of 0.98 g (25 mmoles) of sodium hydride (60% dispersion in mineral oil) in 13 ml of N,N-dimethylformamide was added 3.2 g (20.4 mmoles) of 2-mercapto-1-n-butylimidazole and the mixture stirred at room temperature for a few minutes until the evolution of hydrogen had stopped. The reaction mixture was cooled in an icebath and 3.76 g (26.7 mmoles) of 1-fluoro-4-nitrobenzene was added. The mixture was stirred at 0° C. for 20 minutes and then at room temperature for 3 hours. The reaction was quenched with ice and water to give a total volume of 175 ml. The product was extracted with 3×75ml of dichloromethane. The organics were combined, dried and concentrated. The residual oil was triturated with 50 ml of petroleum ether (bp 30°-60° C.) which was removed by decanting. This process was repeated three times. The remaining oil was dissolved in 200 ml of ether and washed with 100 ml of water. The organic phase was dried and concentrated. The residue was treated with excess 10N hydrogen chloride in ethanol to form the hydrochloride salt. Ether was added and the precipitate collection by filtration and washed with ether. Recrystallization from methanol/ether gave 3.8 (59%) of the product as colorless needles, mp 182°-184° C.

EXAMPLE 13

4-[(1-n-Butyl-1H-imidazol-2-yl)thio]]benzenamine

To a solution of 7.2 g (32 mmoles) of stannous chloride dihydrate in 8.6 ml of concentrated hydrochloric acid, stirred in an ice bath, was added 1.0 g (3.2 mmoles) of the product from Example 12 dissolved in 15 ml of concentrated hydrochloric acid. After stirring at room temperature for 0.5 hours, ice and water were added to the reaction mixture and 3N sodium hydroxide added until the mixture was alkaline. The product was extracted with dichloromethane and the organics were combined dried and concentrated. The residue was crystallized from ether and petroleum ether (bp 30°-60° C.) to give 0.58 g (73%) of the product as off-white prisms, mp 70°-72° C.

EXAMPLE 14

1-Butyl-2-[(4-chlorophenyl)thio]-1H-imidazole hydrochloride

To a solution of 3.0 g (12.1 mmoles) of the product from Example 13 in 30 ml of 3N hydrochloric acid, cooled in an ice bath at −5° C. was added, dropwise, a solution of 0.89 g (12.9 mmoles) of sodium nitrite in 45 ml of water. After stirring for 5 minutes, the reaction mixture was poured into a solution of 2.4 g (24.2 mmoles) of cuprous chloride in 24 ml of concentrated hydrochloride acid. After stirring for 10 minutes, the mixture was heated on a steam bath for 2 hours. After cooling in an icebath, the mixture was made alkaline by the addition of 10N sodium hydroxide. The product was extracted with dichloromethane and the organics combined dried and concentrated. To the residue was added 10N hydrogen chloride in ethanol to form the hydrochloride salt. Ether was added and the precipitate collected by filtration. The product (1.0 g, 30%) was obtained as light tan prisms, mp 143°-148° C. following recrystallization from a mixture of tetrahydrofuran, methanol and ether.

EXAMPLE 15

2-[(2-Chloro-6-nitrophenyl)thio]-1-methyl-1H-imidazole

Starting with 1.92 g (10 mmoles) of 2,3-dichloronitrobenzene and 1.14 g (10 mmoles) of 2-mercapto-1-methylimidazole and following the procedure described in Example 1 there was obtained 2 g (74%) of the product as yellow prisms, mp 102°-104° C.

EXAMPLE 16

3-Chloro-2[-(1-methyl-1H-imidazol-2yl)thio]benzenamine

Starting with 11 g (40 mmoles) of the product from Example 15 and following the procedure described in Example 4, there was obtained 7.6 g (79%) of the product as off-white prisms, mp 123°-124° C.

EXAMPLE 17

2-[(2,6-Dichlorophenyl)thio]-1-methyl-1H-imidazole

Starting with 2.4 g (10 moles) of the product from Example 16 and using the procedure described in Example 14, there was obtained 0.9 g (35%) of the product as off-white prisms mp 113°-115° C.

EXAMPLE 18

2-[(2,6-Dichlorophenyl)thio]-1-methyl-1H-imidazole hydrochloride

The product from Example 17 was treated with hydrogen chloride in ether and dichloromethane to give a 77% yield of the product as colorless prisms, mp 211°-222° C.

EXAMPLE 19

2-[(4-Chloro-2-nitrophenyl)thio]-1-methyl-1H-imidazole

Starting with 1.92g (10 moles) 2,5-dichloronitrobenzene and 1.14 g (10 mmoles) of 2-mercapto-1-methylimidazole and following the procedure described in Example 1 there was obtained 1.0 g (37%) of the product as yellow prisms, mp 143°-145° C.

EXAMPLE 20

2-[(4-Chloro-2-nitrophenyl)thio]-1-methyl-1H-imidazole hydrochloride

The product from Example 19 was treated with hydrogen chloride in dichloromethane and ether to give the product as yellow prisms mp 155°-160° C.

EXAMPLE 21

5-Chloro-2-[(1-methyl-1H-imidazol-2-yl)thio]benzenamine

Starting with 4.1 g (15 mmoles) of the product from Example 19 and using the procedure described in Example 4, there was obtained 2 g (57%) of the product as off-white prisms, mp 127°–129° C.

EXAMPLE 22

2-(2.6-Dichlorophenyl)thio]-1-methyl-1H-imidazole

Starting with 2.4 g (10 mmoles) of the product from Example 21 and using the procedure described in Example 14, there was obtained 1.2 g (46%) of the product as light yellow prisms, mp 79°–80° C.

EXAMPLE 23

2-[(2,4-Dichlorophenyl)thio]-1-methyl-1H-imidazole hydrochloride

Treatment of 0.8g (3.1 mmoles) of the product from Example 22 with hydrogen chloride in ether and dichloromethane gave the product (0.75 g. 76%) which was obtained as off-white prisms, mp 165°–175° C.

EXAMPLE 24

2-[(4-Nitrophenyl)thio]-1-phenyl-1H-imidazole

To a mixture of 0.6 g (13.6 mmoles) of 50% sodium hydride in mineral oil and 8 ml of N,N-dimethylformamide was added 2.0 g (11.4 mmoles) of 2-mercapto-1-phenylimidazole. After stirring for 10 minutes the mixture was cooled in an icebath and 2.1 g (14.8 mmoles) of 1-fluoro-4-nitrobenzene was added. After stirring for 20 minutes, the mixture was warmed to room temperature and stirred for 3 hours. Ice was added and the mixture partitioned between dichloromethane and water. The aqueous phase was separated and extracted with dichloromethane. The organics were dried and concentrated. The residue was recrystallized from dichloromethane/petroleum ether (bp 30°–60° C.) to give 0.9 g (27%) of the product as off-white prisms, mp 123°–125° C.

EXAMPLE 25

2-[(4-Nitrophenyl)thio]-1-phenyl-1H-imidazole hydrochloride

The product from Example 24 was converted to the hydrochloride salt by treatment with ethanolic hydrogen chloride. After recrystallization from methanol/isopropanol/ether the product was obtained off-white prisms, mp 215°–218° C.

EXAMPLE 26

2-[(4-Nitrophenyl)thio]-1H-imidazole

To a mixture of 6.2 g (0.12 mmoles) of sodium methoxide and 90 ml of ethyl alcohol was added 5.8 g (0 058 mmoles) of 2-mercaptoimidazole. After stirring for 0.5 hour, 8.2 g (0.058 mole) of 1-fluoro-4-nitrobenzene was added and the mixture refluxed for 4 hours. The mixture was allowed to cool and filtered to give 5.0 g (39%) of the product. An additional 2.0 g (16%) of product was recovered from the filtrates. Recrystallization from dichloromethane/methanol gave the product as yellow rods. mp 207°–209° C.

EXAMPLE 27

2-[(4-Nitrophenyl)thio]-1H-imidazole hydrochloride

The product from Example 26 was dissolved in methanol and treated with an excess of hydrogen chloride in ethyl alcohol. The mixture was concentrated and the residue triturated with ether and filtered. The solid was recrystallized from methanol to give the product as colorless prisms, mp 235°–240° C. (sealed tube).

EXAMPLE 28

2-[(4-Nitrophenyl)thio]-1-(phenylmethyl)-1H-imidazole

A mixture of 0.85 g (15.8 mmoles) of sodium methoxide and 15 ml of ethanol was refluxed for 5 minutes and then cooled to room temperature. To this solution was added 1.5 g (7.9 mmoles) of 2-mercapto-1-phenylmethylimidazole. After stirring for 10 minutes, 1.1 g (7.9 mmoles) of 1-fluoro-4-nitrobenzene was added and the mixture refluxed for 4 hours. An additional 0.85 g of sodium methoxide was added and the mixture refluxed for 9 hours. The mixture was filtered and the filtrate cooled and the resulting precipitate collected by filtration. The solid was recrystallized from dichloromethane/methanol to give the product as beige prisms, mp 122°–123° C.

EXAMPLE 29

2-[(4-Nitrophenyl)thio]-1-(phenylmethyl)-1H-imidazole hydrochloride

The product from Example 28 was dissolved in mixture of dichloromethane and ethyl alcohol and treated with excess hydrogen chloride in ethyl alcohol. The solvents were removed in vacuo and the residue triturated with ether and filtered. The solid was recrystallized from methanol/ether to give the product as colorless prisms, mp 240°–245° C. (sealed tube).

EXAMPLE 30

1-(4-Nitrophenyl)-2-[(4-nitrophenyl)thio]-1H-imidazole

This product was isolated by a byproduct from the reaction described in Example 26. The compound was obtained as yellow rods after recrystallization from dichloromethane/methanol, mp 173°–175° C.

EXAMPLE 31

2-[(2-Nitrophenyl)thio]-1H-imidazole

A mixture of 5.0 g (0.05 mole) of 2-mercaptoimidazole. 7.9 g (0.05 mole) of 2-chloronitrobenzene, 6.5 g (0.12 mole) of sodium methoxide and 150 ml of ethanol was stirred and refluxed for 5 hours. An additional 0.8 g of 2-chloronitrobenzene, was added and refluxing continued for 5 more hours. The mixture was filtered hot and the filtrates concentrated. The residue was partitioned with water and dichloromethane. The undissolved solid was collected by filtration to give 8.3 g of product. The dichloromethane was dried and concentrated. The residue was recrystallized from dichloromethane to give an additional 1.2 g of product. The total yield was 87% and the product was obtained as yellow rods, mp 178°–181° C.

EXAMPLE 32

2-[(2-Aminophenyl)thio]-1H-imidazole

To a solution of 8.0 g (37.6 mmoles) of the product from Example 31 in 80 ml of glacial acetic acid was added to a solution of 25.5 g (113 mmoles) of stannous chloride dihydrate in 40 ml of 6N hydrochloric acid. The mixture was allowed to stir at room temperature overnight and then concentrated to a small volume. Ice was added and the solution made basic by the addition of 10N sodium hydroxide. The mixture was filtered and the solid washed with water. The filtrates were extracted with dichloromethane, washed with water, dried and concentrated. The residue was treated with ether, cooled and the solid collected by filtration to give 2.5 g of the product. The aqueous solution was adjusted to pH 9 with hydrochloric acid and filtered. The solid was stirred with methanol and then with methanol/dichloromethane. After filtration the filtrates were used to extract all of the aqueous layers. The organics were dried and concentrated to give an additional 3.5 of product. The product (83%) was obtained as colorless prisms, mp 135°–137° C.

EXAMPLE 33

2-[(2-Chlorophenyl)thio]-1H-imidazole

To a solution of 5.6 g (29.3 mmoles) of the product from Example 32 in 50 ml of 3N hydrochloric acid and 50 ml of glacial acetic acid (cooled in an ice bath), was added dropwise over 20 minutes, a solution of 2.0 g (29.3 mmoles) of sodium nitrite in 8 ml of water. After stirring for 10 minutes, the mixture was added to a cold solution of 8.7 g (80 mmoles) cuprous chloride in 80 ml of 6N hydrochloric acid. After stirring at room temperature for 5 hours, the mixture was concentrated and the residue made alkaline with ammonium hydroxide. The product was extracted with dichloromethane which was washed with saturated sodium chloride, dried and concentrated. The residue was dissolved in hot dichloromethane and filtered through silica gel using dichloromethane/ethyl acetate (1:1 by volume) as the eluent. The fractions containing the product were concentrated to give 4.9 g (79%) of the product which was crystallized from dichloromethane to give colorless rods, mp 138°–141° C.

EXAMPLE 34

2-[(2-Chlorophenyl)thio]-1H-imidazole hydrochloride

A solution of the product from Example 33 in methanol was treated with an excess of hydrogen chloride in ethyl alcohol. The mixture was concentrated in vacuo and the residue triturated with ether and filtered. The solid was recrystallized from methanol/ether to give the product as colorless prisms, mp 189°–192° C. (sealed tube).

EXAMPLE 35

2-[(4-Methoxy-2-nitrophenyl)thio]-1-methyl-1H-imidazole

To a mixture of 2-mercapto-1-methylimidazole (1.14 g, 10 mmoles), 0.6 of 60% sodium hydride in mineral oil and 20 ml of N,N-dimethylformamide was added 1.88 g (10 mmoles) of 4-chloro-3-nitroanisole. The mixture was stirred at room temperature for 0.5 hours and then heated at 90°–100° C. for 4 hours. After cooling in an icebath, 0.5 ml of acetic acid was added and the mixture was partitioned between dichloromethane and dilute sodium bicarbonate. The organics were concentrated on a steam bath to a small volume and the residue was chromatographed on silica gel using ethyl acetate as the eluent. The fractions containing the product were combined and concentrated to give 1.0 g (38%) of the product, mp 117°–120° C.).

EXAMPLE 36

2-[(4-Nitrophenyl)thio]pyrimidine

A mixture of 1.12 g (10 mmoles) of 2-mercaptopyrimidine, 1.4 (10 mmoles) of 1-fluoro-4-nitrobenzene, 0.5 of potassium hydroxide and 10 ml of dimethylsulfoxide were heated at 120°–130° C. for 6 hours and then cooled. After pouring into a mixture of ice, water and sodium chloride the mixture was allowed to stand for 30 minutes and then filtered. The solid was washed with water, air dried and chromatographed on silica gel using ethyl acetate/hexane (1:1 by volume) as the eluent. The fractions containing the product were combined and concentrated to give 1 g (43%) of the product as yellow rods, mp 103°–104° C.

EXAMPLE 37

4-[(2-pyrimidinyl)thio]benzenamine

Using the procedure described in Example 4 and starting with 2.4 g (10 mmoles) of the product from Example 36, there was obtained 0.8 g (40%) of the product as yellow prisms, mp 124°–126° C.

EXAMPLE 38

2-[(4-Chlorophenyl)thio]pyrimidine

Using the procedure described in Example 6 and starting with 3.05 g (15 mmoles) of the product from Example 37, there was obtained 1.5 g (45%) of the product as yellow prisms, mp 68°–70° C.

EXAMPLE 39

2-[(2-Chloro-4-methoxyphenyl)thio]-1-methyl-1H-imidazole hydrochloride

The product from Example 35 was converted to the corresponding amino compound by reduction of the nitro group with stannous chloride following the procedure described in Example 4. The amino compound was obtained in 16% yield as colorless rods, mp 139°–140° C. The amino group was converted to a chloro group by diazotization following the procedure given in Example 6, Method A. The product was converted to the hydrochloride salt by treatment with gaseous hydrogen chloride in ether and obtained as light yellow prisms, mp 178°–183° C. The yield from the amino compound was 61%.

EXAMPLE 40

2-[(3,4-Dimethoxyphenyl)thio]-1-methyl-1H-imidazole hydrochloride

A solution of 1 g (14.4 mmoles) of sodium nitrite in 7 ml of water was added dropwise to a solution of 2.0 g (13.1 mmoles) of 4-aminoveratrole in 65 ml of 1N sulfuric acid. The reaction was carried out under nitrogen in an icebath. The resulting solution was added dropwise to a mixture of 1.4 g (13.1 mmoles) of 2-mercapto-1-methylimidazole and 0.7 g of cupric oxide in 45 ml of 1N sulfonic acid, cooled in an icebath. After stirring for 1 hour, the icebath was removed and the mixture stirred overnight at room temperature. Ether and ammonium hydroxide were added and the mixture filtered. The filtrates were separated and the aqueous fraction extracted with ether. The organics were combined, dried and concentrated in vacuo. Ethanolic hydrogen chloride was added to the residue and the mixture concentrated. The product was recrystallized from 2-propanol and then from methanol/ether and obtained as colorless rods (21% yield), mp 194°–196° C. (sealed tube).

EXAMPLE 41

2[(2-Chlorophenyl)sulfinyl]-1H-imidazole

To a solution of 2.0 g (9.5 mmoles) of the product from Example 33 in 250 ml of dichloromethane, cooled in an icebath, was added over 15 minutes, 2.3 g (11.4 moles) of 85% meta-chloroperbenzoic acid. The mixture was allowed to stand for 3 days and then quenched by the addition of dilute ammonium hydroxide. Filtration yielded 0.2 g of the product. The filtrates were separated and the aqueous extracted with dichloromethane. The filtrates were dried and concentrated to give an additional 1.0 of product. The aqueous extracts were acidified with acetic acid and then made basic with sodium bicarbonate. After extracting with dichloromethane the organics were combined and concentrated to give 0.9 g of product. All of the solids were combined and recrystallized from dichloromethane/methanol to give 1.5 g (70%) of the product as colorless rods, mp 188°-190° C.

EXAMPLE 42

2-[(2-Chlorophenyl)sulfonyl]-1H-imidazole

To a suspension of 3.5 g (15.4 mmoles) of the product from Example 41 in 500 ml of dichloromethane was added 3.8 g (18.5 moles) of 85% meta-chloroperbenzoic acid. After stirring for 5 hours at room temperature, the reaction was quenched with sodium bicarbonate solution. The layers were separated and the aqueous extracted with dichloromethane. The organics were combined, dried and concentrated in vacuo. Petroleum ether (bp 30°-60° C.) was added and the mixture filtered. The solid was recrystallized from dichloromethane/ methanol/ether to give 3.5 (93%) of the product as colorless needles, mp 204°-207° C.

EXAMPLE 43

2-[(2-Chlorophenyl)sulfinyl]-1-methyl-1H-imidazole

To a solution of 0.9 g (4 mmoles) of the product from Example 6 in 80 ml of dichloromethane was added 0.8 g (4.7 mmoles) of 85% meta-chloroperbenzoic acid over a period of 5 minutes. After stirring for 2 hours the reaction was quenched by the addition of dilute ammonium hydroxide with vigorous stirring. The layers were separated and the organics dried and concentrated. The residue was triturated with 10 ml of ether and filtered to give 0.6 g (62%) of the product as off-white prisms, mp 132°-134° C.

EXAMPLE 44

2-[(2-Chlorophenyl)sulfonyl]-1-methyl-1H-imidazole

To a stirred solution of 0.9 g (4 mmoles) of the product from Example 6 in 80 ml of dichloromethane was added 1.6 g (9 mmoles) of meta-chloroperbenzoic acid. After stirring overnight, an additional 1.6 g of the per acid was added followed by an additional 1.6 g after stirring for 1 hour. After stirring for 15 minutes the layers were separated and the organics dried and concentrated to give 1.1 g (100%) of the product as off-white prisms, mp 156°-159° C.

EXAMPLE 45

2[[4-(Trifluoromethyl)phenyl]thio]-1-methyl-1H-imidazole hydrochloride

A mixture of 11 g (50 mmoles) of 4-trifluoromethyl-1-bromobenzene, 5.7 g (50 mmoles) of 1-methyl-2-mercaptoimidazole, 4 g of potassium hydroxide and 100 ml of dimethylsulfoxide was heated at 130°-140° C. for 16 hours and then cooled. The mixture was poured over a mixture of ice and sodium chloride and extracted with dichloromethane. The organics were dried, concentrated and the residue chromatographed on silica gel using ethyl acetate as the eluent. The residue was treated with an excess of hydrogen chloride in ether to form the hydrochloride salt. The salt which precipitated was collected by filtration, washed with ether and dried to give 3.2 g (22%) of the product as off-white prisms, mp 180°-188° C.

EXAMPLE 46

2-[(2-Chlorophenyl)thio]-1-(1,1-dimethylethyl)-1H-imidazole

The procedure given in Example 6, Method B, was used to prepare this product starting with 0.3 g (1.9 mmoles) of 1-(1,1-dimethylethyl)-2-mercaptoimidazole and 0.24 g (1.9 mmoles) of 2-chloroaniline. In this case the reaction time was extended to 18 hours. The crude product was chromatographed through silica gel using dichloromethane and then a mixture of dichloromethane/ether (8:1 by volume) as the eluent. The fractions containing the product were combined and concentrated. The residue was recrystallized from ether/petroleum ether (bp 30°-60° .C) to give 0.2g (39%) of the product as off-white prisms, mp 97°-99° C.

EXAMPLE 47

2-[(2-Chlorophenyl)thio]-1-(1,1-dimethylethyl)-1H-imidazole hydrochloride

The product obtained in Example 46 was converted to the hydrochloride salt using hydrogen chloride in ethanol. The crude product was recrystallized from 2-propanol/ether to give the salt (20%) as off-white prisms, mp 173°-175° C. (sealed tube).

EXAMPLE 48

2-[(2-Chlorophenyl)thio-1-octyl-1H-imidazole hydrochloride

To a solution of 0.3 g (1.42 mmoles) of the product from Example 33 in 2 ml of dry N,N-dimethylformamide was added 0.18 g (1.56 mmoles) of potassium t-butoxide with stirring and under nitrogen. After stirring for 20 minutes the reaction was cooled in an icebath and 0.33 g (1.70 mmoles) of 1-bromooctane was added. The mixture was stirred for 15 minutes and then warmed to room temperature and stirred for 18 hours. The mixture was partitioned between ether and water. The organics were combined, washed with sodium chloride solution, dried and concentrated. The crude product was converted to the hydrochloride salt by the addition of ethanolic hydrogen chloride. The solution was concentrated to dryness and the residue recrystallized from 2-propanol/ether to give the salt as colorless needles (0.25 g, 49%), mp 114°-116° C.

EXAMPLE 49

2-[(3-Chloro-6-nitrophenyl)thio]-1-methyl-1H-imidazole

To a solution of 10 g (87.7 mmoles) of 2-mercapto-1-methylimidazole in 300 ml of ethanol was added 10.4 g (193 mmoles) of sodium methoxide followed by 20.8 g (92.1 mmoles) of 1-chloro-3,4-dinitrobenzene. The mixture was stirred and refluxed for 8 hours. An additional 3 g of sodium methoxide was added and refluxing was continued for 5 more hours. The mixture was filtered hot and the filtrates concentrated in vacuo. The residue was partitioned between dichloromethane and water. The organics were dried and concentrated. The residue was recrystallized from dichloromethane and methanol to give 12.5 g (53%) of the product as yellow prisms, mp 130°-131° C.

EXAMPLE 50

4-Chloro-2-[(1-methyl-1H-imidazol-2-yl)thio]benzenamine

A mixture of 3.0 g (10.7 mmoles) of the product from Example 49, 1.5 spatulas of Raney nickel and 200 ml of ethanol was hydrogenated at 1 atmosphere and room temperature for 18 hours. An additional spatula of Raney nickel was added and hydrogenation continued for 90 minutes. The mixture was filtered to remove the catalyst and the filtrates concentrated. The residue was recrystallized from dichloromethane/petroleum ether (bp 30°-60° C.) to give the product as colorless plates (1.7 g, 66%), mp 116°-120° C.

EXAMPLE 51

2-[(2,5-Dichlorophenyl)thio]-1-methyl-1H-imidazole

From a large scale preparation of the product described in Example 6, Method A, there was isolated the current product as a minor component (yield 1%) by column chromatography. The product was obtained as yellow prisms, mp 66°-67° C.

EXAMPLE 52

2-[(2-Chloro-4-nitrophenyl)thio)-1-methyl-1H-imidazole

To 18 ml of concentrated sulfuric acid stirred in an icebath, was added in portions, 1.5 g (6.7 mmoles) of the product obtained in Example 6. After the addition was complete, potassium nitrate (0.63 g, 6.3 mmoles) was added in portions keeping the temperature between 0° and 5° C. After stirring in an icebath for 2 hours, the reaction mixture was poured over ice and made basic with concentrated ammonium hydroxide. The mixture was extracted with dichloromethane. The organics were combined, washed with water, dried and concentrated. The residue was dissolved in 200 ml of refluxing ether, treated with charcoal and filtered. The filtrate was concentrated to 50 ml and then cooled. The resulting solid was collected by filtration to give 0.64 g of product. The filtrate was diluted with petroleum ether (bp 30°-60° C.) and filtered to give an additional 0.28 g of the product. The total yield was 51% and the product was obtained as yellow-green needles, mp 127°-129° C.

EXAMPLE 53

3-Chloro-4-[(1-methyl-1H-imidazol-2-yl)thio]benzenamine

The product from Example 52 was reduced with stannous chloride following the procedure described in Example 4. The product was recrystallized from dichloromethane/hexane and obtained as off-white prisms (yield 81%), mp 122°-123° C.

EXAMPLE 54

2-[(2-Chloro-4-iodophenyl)thio]-1-methyl-1H-imidazole

To a solution of 0.49 g (2 mmoles) of the product from Example 53 in 4.8 ml of 3N hydrochloric acid and 4.8 ml of glacial acetic acid, stirred in an icebath, was added dropwise a solution of 0.16 g (2.3 mmoles) of sodium nitrite in 1.5 ml of water keeping the temperature at 0°-5° C. After stirring for 10 minutes, a solution of 0.69 g (4.2 mmoles) of potassium iodide in 2.1 ml of water was added with vigorous stirring, again keeping the temperature below 5° C. The mixture was stirred in the cold for 1 hour and then at room temperature for 3 hours. After pouring over ice the mixture was made basic with 40% sodium hydroxide, keeping the temperature below 10° C. The mixture was extracted with ethyl acetate which was dried and concentrated. The residue was triturated with hot ether and filtered to remove some insoluble material. The ether was concentrated in vacuo and the residue chromatographed on silica gel using dichloromethane/ethyl acetate (9:1 by volume) as the eluent. The fractions containing the product were concentrated and the product purified by recrystallization from ether/petroleum ether (bp 30°-60° C.). The yield was 0.32 g (46%) and the product was obtained as colorless prisms, mp 99°-101° C.

EXAMPLE 55

2-[(4-Fluoro-2-nitrophenyl)thio]-1-methyl-1H-imidazole

To a mixture of 0.6 g of 60% sodium hydride in mineral oil in 25 ml of N,N-dimethylformamide was added 1.1 g (10 mmoles) of 2-mercapto-1-methylimidazole. After stirring for 30 minutes, 1.6 g (10 mmoles) of 2,5-difluoronitrobenzene was added and the mixture stirred at room temperature for 16 hours. After adding 0.5 ml of acetic acid, the mixture was poured into a mixture of ice, water and sodium chloride. After standing for 1 hour the solid was collected by filtration, washed with water and dried. The crude product was purified by chromatography on silica gel using ethyl acetate as the eluent. The fractions containing the product were combined and concentrated to give 0.7 g (28%) of the product as yellow prisms, mp 123°-126° C.

EXAMPLE 56

2-[(2-Fluoro-4-nitrophenyl)thio]-1-methyl-1H-imidazole

This product was prepared starting with 3,4-difluoronitrobenzene and using the procedure described in Example 5. The product was obtained in 24% yield after column chromatography and obtained as yellow prisms, mp 97°-99° C.

EXAMPLE 57

2-[(4-Trifluoromethyl)-2-nitrophenyl]thio-1-methyl-1Himidazole

To a suspension of 0.6 g of sodium hydride (60% dispersion in mineral oil) in 25 ml of N,N-dimethylformamide was added 1.15 g (10 mmoles) of 2-mercapto-1-methylimidazole. The mixture was stirred at room temperature for 30 minutes and then 2.3 g of 4-chloro-3-nitrobenzotrifluoride was added. After stirring at room temperature for 18 hours, the mixture was poured into a mixture of ice, water, sodium chloride, and acetic acid. The resulting precipitate was collected by filtration, washed with water and air dried. The crude product was purified by column chromatography on silica gel using ethyl acetate as the eluent. The fractions containing the product were combined and concentrated to give 2.3 g (76%) of the product as yellow prisms, mp 123°-125° C.

EXAMPLE 58

5-(Trifluoromethyl)-2-[(1-methyl-1H-imidazol-2-yl)thio]benzenamine

The compound obtained from Example 57 was converted to the product of this example using the procedure described in Example 53. The product was obtained in 73% yield and obtained as off-white prisms, mp 112°-114° C.

EXAMPLE 59

2-[[2-Chloro-4-(trifluoromethyl)phenyl]thio]-1-methyl-1Himidazole hydrochloride

The amino compound from Example 58 was converted to the corresponding chloro compound in 38% yield employing the procedure described in Example 6, Method A, and converted to the hydrochloride salt using the procedure of Example 7. The product was obtained as off-white prisms, mp 175°-185° C.

EXAMPLE 60

2-[[2-(Trifluoromethyl)-4-nitroohenyl]thio]-1-methyl-1Himidazole

This product was prepared starting with 2-chloro-5nitrobenzotrifluoride using the procedure described in Example 57 and obtained in 73% yield. The product, after purification, was obtained as light yellow prisms, mp 98°-100° C.

EXAMPLE 61

3-(Trifluoromethyl)-4-[(1-methyl-1H-imidazol-2-yl)thio]benzenamine

This product was prepared using the procedure described in Example 53 starting with the product from Example 60. The product was obtained as light yellow prisms (62% yield), mp 91°-93° C.

EXAMPLE 62

2-[[4-Chloro-2-(trifluoromethyl)phenyl]thio]-1-methyl-1Himidazole hydrochloride

This product was prepared starting with the compound obtained in Example 61 and using the procedure described in Example 6, Method A, and converted to the hydrochloride salt using the procedure of Example 7. The product was obtained as off-white prisms, mp 163°-166° C.

EXAMPLE 63

2[[2-(Trifluoromethyl)phenyl]thio]thiazole hydrochloride

To a solution of 3.22g (20 mmoles) of 1-amino-2-trifluoromethylbenzene in 90 ml of 1N sulfuric acid, was added dropwise a solution of 1.45 g (21 mmoles) of sodium nitrite in 10 ml of water. The reaction was stirred in an ice bath and the temperature was kept below 5° C. during the addition. This mixture was then added dropwise to a mixture of 2.34 g (20 mmoles) of 2-mercaptothiazole and 1 g of cuprous oxide in 70 ml of 1N sulfuric acid, stirred in an icebath. The reaction was allowed to slowly warm to room temperature and stirred overnight. The mixture was partitioned with ammonium hydroxide and ether, the organics were combined, washed with brine, dried and concentrated. The residue was chromatographed on silica gel using hexane/ether (2:1 by volume) as the eluent. The residue was converted to the hydrochloride salt by treatment with dry hydrogen chloride in ether. The solid was collected by filtration and recrystallized from ethyl acetate to give 1.3 g (22%) of the product as off-white needles, mp 149°-152° C.

EXAMPLE 64

TABLET FORMULATION (Wet Gramulation)

| Item | Ingredient | mg/tablet | | |
|---|---|---|---|---|
| | | 100 mg | 500 mg | 1000 mg |
| 1 | 2-[(4-chlorophenyl)thio]-1-methyl-IH-imidazole | 100 | 500 | 1000 |
| 2. | Lactose | 132 | — | — |
| 3. | Pregelantinized Starch | 16 | 30 | 50 |
| 4. | Modified Starch | 30 | 40 | 50 |
| 5. | Magnesium Stearate | 2 | 6 | 8 |
| | Total | 280 | 576 | 1108 |

Manufacturing Procedure
1. Mix items 1, 2. 3 and 4 and granulate with water.
2. Dry the granulation at 50° C.
3. Pass the granulation through suitable milling equipment.
4. Add Item 5 and mix for three minutes; compress on a suitable press.

EXAMPLE 65

CAPSULE FORMULATION

| Item | Ingredient | mg/tablet | | | |
|---|---|---|---|---|---|
| 1. | 2-[(4-chlorophenyl)thio]-1-methyl-IH-imidazole | 25 | 50 | 100 | 500 |
| 2. | Lactose Hydrous | 143 | 168 | 148 | — |
| 3. | Corn Starch | 20 | 20 | 40 | 70 |
| 4. | Talc | 10 | 10 | 10 | 25 |
| 5. | Magnesium Stearate | 2 | 2 | 2 | 5 |
| | Total | 200 | 250 | 300 | 600 |

Manufacturing Procedure
1. Mix items 1, 2 and 3 in a suitable mixer for 30 minutes.
2. Add items 4 and 5 and mix for 3 minutes.
3. Fill into suitable capsules.

EXAMPLE 66

WET GRANULATION FORMULATION

| Item | Ingredient | mg/tablet | |
|---|---|---|---|
| 1. | 2-[(4-chlorophenyl)thio]-1-methyl-IH-imidazole | 25 | 50 |
| 2. | Polyvinyl Pyrrolidone | 5 | 10 |
| 3. | Lactose Anhydrous DTG | 133 | 142 |
| 4. | Avicel PH 102 | 25 | 30 |
| 5. | Modified Starch | 10 | 15 |
| 6. | Magnesium Stearate | 2 | 3 |
| | Total | 200 | 250 |

Manufacturing Procedure
1. Dissolve item 2 in water.
2. Mix items 1, 3, 4 and 5 in a suitable mixer and granulate with solution in Step 1.
3. Dry overnight at 45° C., screen through #20 mesh and add Item 6 and mix. Compress on a suitable press.

EXAMPLE 67

Cream 5%

The following is the quantitative composition of drug:

| Ingredient | g/kg | Reasonable Variations |
|---|---|---|
| 2-[(4-chlorophenyl(thio]-1-methyl-IH-imidazole | 51.50* | — |
| Glyceryl Monostearate S.E.[1] | 100.00 | 80–120 |
| Polysorbate 60[2] | 20.00 | 15–25 |
| Cetyl Alcohol | 50.00 | 40–60 |

| Ingredient | g/kg | Reasonable Variations |
|---|---|---|
| Petrolatum | 70.00 | 50–90 |
| Methylparaben | 1.50 | 1.25–1.75 |
| Propylparaben | 0.50 | 0.4–0.6 |
| Propylene Glycol | 200.00 | 150–250 |
| Purified Water | 521.70 | 475–575 |
| Total | 1015.20 | |

1. The items are placed in a suitable mixer according to known procedures and a homogenous cream is prepared.
*3% excess
¹Arlacel 165
²Tween 60

EXAMPLE 68

SOFT GELATIN FORMULATION

| Item | Ingredient | mg | capsule |
|---|---|---|---|
| 1. | 2-[(4-chlorophenyl)thio]-1-methyl-IH-imidazole | 50 | 250 |
| 2. | PEG 400 | 325 | 550 |
| 3. | MCM 90 | 100 | 150 |
| 4. | Tween 80 | 25 | 50 |
| | Total | 500 | 1000 |

Manufacturing Procedure:
1. Dissolve item 1 in item 2.
2. Add item 3 and mix well.
3. Add item 4 and mix well until dissolved.
4. Fill in soft gelatin capsules.

We claim:

1. A compound of the formula

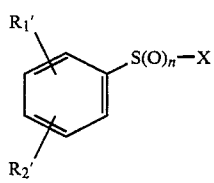

I wherein, n is an integer of 0 to 2; one or both of $R_1'$ and $R_2'$ are, independently, halogen, trifluoromethyl or lower alkoxy; and X is

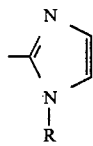

where R is hydrogen, lower alkyl, phenyl or phenyl bearing one or two substituents independently selected from the group consisting of halogen, lower alkylamino and di-lower alkylamino, or phenyl-lower alkyl or phenyl-lower alkyl bearing one or two substituents on the phenyl moiety independently selected from the group consisting of halogen, trifluoromethyl, lower alkyl, lower alkoxy, nitro, amino, lower alkylamino and di-lower alkylamino, or a pharmaceutically acceptable acid addition salt thereof.

2. A compound, in accordance with claim 1, wherein one or both of $R_1'$ and $R_2'$ are, independently, halogen or trifluoromethyl and X is

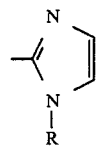

wherein R is lower alkyl.

3. A compound, in accordance with claim 1, 2-[(2-chlorophenyl)thio]-1H-imidazole.

4. A compound, in accordance with claim 1, 2[(4-chlorophenyl)thio]-1H-imidazole.

5. A pharmaceutical composition containing an effective amount of a compound of the formula

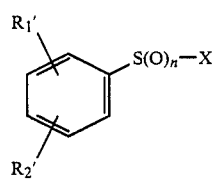

I wherein n is an integer of 0 to 2; one or both of $R_1'$ and $R_2'$ are, independently, halogen, X trifluoromethyl or lower alkoxy; and is

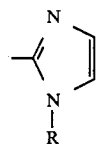

wherein R is hydrogen, lower alkyl, phenyl or phenyl bearing one or two substituents independently selected from the group consisting of halogen, lower alkylamino and di-lower alkylamino, or phenyl-lower alkyl or phenyl-lower alkyl bearing one or two substituents on the phenyl moiety independently selected from the group consisting of halogen, trifluoromethyl, lower alkyl, lower alkoxy, nitro, amino, lower alkylamino and di-lower alkylamino, or a pharmaceutically acceptable acid addition salt thereof, and an inert carrier.

6. A pharmaceutical composition, in accordance with claim 5, wherein one or both of $R_1'$ and $R_2'$ are, independently, halogen or trifluoromethyl and X is

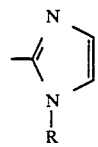

wherein R is lower alkyl.

7. A method of treating an inflammatory disease which comprises administering to a host requiring such treatment an effective amount of a compound of the formula

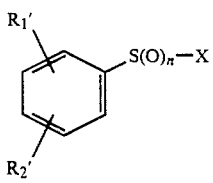

wherein n is a integer 0 to 2; one or both of $R_1'$ and $R_2'$ are, independently, halogen, trifluoromethyl or lower alkoxy; and X is

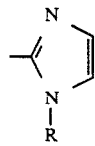

wherein R is hydrogen, lower alkyl, phenyl or phenyl bearing one or two substituents independently selected from the group consisting of halogen, lower alkylamino and di-lower alkylamino, or phenyl-lower alkyl or phenyl-lower alkyl bearing one or two substituents on the phenyl moiety independently selected from the group consisting of halogen, trifluoromethyl, lower alkyl, lower alkoxy, nitro, amino, lower alkylamino and di-lower alkylamino, or a pharmaceutically acceptable acid addition salt thereof.

8. A method, in accordance with claim 7, wherein one or both of $R_1'$ and $R_2'$ are, independently, halogen or trifluoromethyl and X is

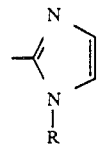

wherein R is lower alkyl.

9. A method, in accordance with claim 7, wherein the compound is 2-[(2- chlorophenyl)thio]-1H-imidazole.

10. A method, in accordance with claim 7, wherein the compound is 2-[(4-chlorophenyl)thio]-1H-imidazole.

11. A method, in accordance with claim 7, wherein the compound is 2-[(4-chlorophenyl)thio]pyrimidine.

* * * * *

UNITED STATES PATENT AND TRADEMARK OFFICE
CERTIFICATE OF CORRECTION

PATENT NO. : 4,973,599  Page 1 of 2
DATED : November 27, 1990
INVENTOR(S) : Norman Washburn Gilman and Wen Yean Chen It is certified that error appears in the above-identified patent and that said Letters Patent is hereby corrected as shown below:

The Title page should be deleted to appear as per attached Title page.

Claim 5, Column 26, line 29, delete the X.

Claim 5, Column 26, line 30, "and is" should be --- and X is ---.

Claim 11 should be cancelled

Signed and Sealed this

Twenty-fifth Day of May, 1993

Attest:

MICHAEL K. KIRK

Attesting Officer    Acting Commissioner of Patents and Trademarks

PHENYLTHIOHETEROCYCLIC DERIVATIVES

Inventors: Norman W. Gilman, Wayne; Wen Y. Chen, Nutley, both of N.J.

Assignee: Hoffmann-La Roche Inc., Nutley, N.J.

Appl. No.: 323,583

Filed: Mar. 14, 1989

Int. Cl.$^5$ .................. C07D 233/84; A61K 31/415
U.S. Cl. .................. 514/398; 514/274; 514/369; 548/337; 548/182; 548/186; 544/315; 544/318
Field of Search .................. 514/274, 369, 398; 544/315, 318; 548/182, 186, 337

References Cited
PUBLICATIONS

Noguchi et al., Chemical Abstracts, vol. 70, Entry 77873q (1969).
Henry, Chemical Abstracts, vol. 68, Entry 1051952 (1968).
Niedballa et al., Chemical Abstracts, vol. 96, Entry 181284w (1982).
van Zwieten et al., Chemical Abstracts, vol. 57, Entry 12464h (1962).
van Zwieten et al., C.A. 57; 16547f (1962).
van Zwieten et al., C.A. 57: 17134(c) (1962).
Bouin-Roubaud et al., Can. J. Chem. vol. 59, pp. 2883–2890 (1981).
Delarge et al., Eur. J. Med. Chem. Chim. Ther., (1984) 19 No. 6, 559–565.

*Primary Examiner*—John M. Ford
*Attorney, Agent, or Firm*—George M. Gould; Bernard S. Leon; William G. Isgro

ABSTRACT

Compounds of the formula

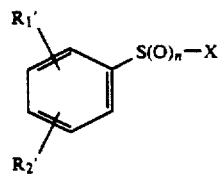

I wherein n is a integer of 0 to 2; $R_1'$ and $R_2'$ are, independently, hydrogen, halogen, trifluoromethyl, lower alkoxy or lower alkyl; and X is pyrimidinyl, thiazolyl or

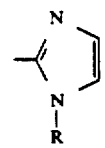

wherein R is hydrogen, lower alkyl, aryl or ar-lower alkyl; provided that at least one or $R_1'$ and $R_2'$ is other than hydrogen,
and their pharmaceutically acceptable acid addition salts, and an anti-inflammatory method utilizing a compound of the formula

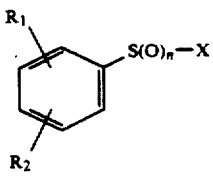

II wherein n is an integer of 0 to 2; $R_1$ and $R_2$ are, independently, hydrogen, halogen, trifluoromethyl, nitro, amino, lower alkylamino, di-lower-alkylamino, lower alkoxy or lower alkyl; and X is pyrimidinyl, thiazolyl or

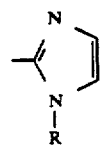

wherein R is hydrogen, lower alkyl, aryl or ar-lower alkyl;
and their pharmaceutically acceptable acid addition salts, are described.

10 Claims, No Drawings